United States Patent [19]

Fox

[11] Patent Number: 4,476,027

[45] Date of Patent: Oct. 9, 1984

[54] USE OF MAGNETIC SEPARATION IN SCAVENGING HYDROGEN SULFIDE

[75] Inventor: Irwin Fox, Ballwin, Mo.

[73] Assignees: Alvin Samuels, New Orleans, La.; David Samuels, St. Louis, Mo. ; part interest to each

[21] Appl. No.: 406,297

[22] Filed: Aug. 9, 1982

Related U.S. Application Data

[63] Continuation-in-part of Ser. No. 221,897, Dec. 31, 1980, Pat. No. 4,344,842.

[51] Int. Cl.$^3$ .................... B01D 15/00; C09K 7/04
[52] U.S. Cl. ................... 210/695; 423/231; 204/155; 210/713; 210/916; 209/8; 208/244
[58] Field of Search ............ 423/231, 221, 151; 204/155; 175/64–66, 206; 210/222, 223, 695, 722, 749; 209/8; 252/8.5 E, 8.55 B, 8.55 E; 208/244

[56] References Cited

U.S. PATENT DOCUMENTS

| | | | |
|---|---|---|---|
| 2,276,075 | 3/1942 | Wuensch | 175/66 |
| 4,008,775 | 2/1977 | Fox | 175/64 |
| 4,269,279 | 5/1981 | House | 175/66 |
| 4,324,298 | 4/1982 | Fox | 423/231 |
| 4,344,842 | 8/1982 | Fox | 208/244 |

OTHER PUBLICATIONS

Garrett et al., "Chemical Scavengers for Sulfides in Water-Base Drilling Fluids", Journal of Petroleum Technology, vol. XXXI, June 1979, pp. 787–796.

Ray et al., "Use of Reactive Iron Oxide to Remove H$_2$S From Drilling Fluid", Journal of Petroleum Technology, vol. XXXI, June 1979, pp. 797–801.

*Primary Examiner*—Earl C. Thomas
*Attorney, Agent, or Firm*—Jerome A. Gross

[57] ABSTRACT

Use of ferri-magnetic reactive iron oxide particles to react hydrogen sulfide in water, hydrocarbon liquids or drilling mud affords quick, effective scavenging of these liquids without accumulation of particulate matter and without wasting the reactive particles. The reaction product is environmentally safe, so that it may be disposed of on a simple waste heap.

A quantity of the magnetic iron oxide particles, principally a synthetic porous Fe$_3$O$_4$, is suspended in the liquid. The quantity added is in excess of that required for the reaction with the hydrogen sulfide in order to speed the reaction time and provide a large margin of safety. In use, the reactive iron oxide particles contact and react the hydrogen sulfide, forming a non-magnetic particulate product of reaction. Thus, if used to scavenge a drilling mud, this contact and reaction occurs as the mud, bearing the drill cuttings, rises through the drilling formation.

By passing the liquid, or at least that portion of it which includes all particulate matter, through a magnetic separator, substantially all, or at least the greater part of, the unreacted oxide particles are recovered for re-use. Since the unreacted particles are characterized by low remanent magnetism, after the magnetic separation they are readily re-suspended in such liquid.

2 Claims, No Drawings

USE OF MAGNETIC SEPARATION IN SCAVENGING HYDROGEN SULFIDE

CROSS REFERENCE TO RELATED APPLICATIONS

The present invention is a continuation in part of co-pending application, Ser. No. 06/221,897 filed Dec. 31, 1980, now U.S. Pat. No. 4,344.842, entitled "Reactive Iron Oxide Agents for Scavenging Hydrogen Sulfide from Hydrocarbon Liquids" and as to common subject matter, the data of that application is claimed.

TECHNICAL FIELD

This invention relates to scavenging hydrogen sulfide, as encountered in well drilling or in waste or geothermal water or hydrocarbon oil, by use of an excess quantity of magnetic iron oxide particles; the excess is magnetically separated for re-use.

BACKGROUND ART

Hydrogen sulfide is often present in drilling formations and is a by-product of some chemical processes. Wherever encountered, it is a contaminate that must be eliminated.

Hydrogen sulfide encountered in drilling oil or gas wells may be dangerous or even deadly. It may be scavenged by additives to the drilling mud. One such additive and the process of using it is disclosed in U.S. Pat. No. 4,008,775.

In my co-pending application, Ser. No. 06/221,897, it is disclosed that such an additive may be added directly to hydrocarbon oil contaminated by hydrogen sulfide, the scavenging taking place in the oil without any other medium.

The additive so utilized is a unique iron oxide particle characterized by an $Fe_3O_4$ crystalline phase but including an amorphous $Fe_2O_3$ moiety; on reaction with hydrogen sulfide an environmentally safe reaction product is formed which is substantially acid stable. The reaction product is non-magnetic, whereas the unreacted particles are attracted to a magnet. When used as a drilling mud additive, the extent to which the particles have been exhausted has been monitored by magnetic differentiation.

DISCLOSURE OF THE INVENTION

The present invention is a process utilizing the described iron oxide particles to scavenge hydrogen sulfide by suspension in contaminated liquids such as water, hydrocarbon liquids or drilling mud. Utilization of this process provides effective, safe and speedy hydrogen sulfide scavenging without accumulation of particulate matter in the liquid and without wasting the reactive particles.

The reactive iron oxide particles employed are considered to be ferri-magnetic, in the sense that, while they are attracted to a magnet, they retain little remanent magnetism. Thus, once magnetically separated, they do not attract one another and may be readily re-suspended. Uniquely, these ferri-magnetic iron oxide particles react with hydrogen sulfide to form a substantially non-magnetic environmentally safe particulate product of reaction. Thus, an excess quantity over that required for scavenging is used in the suspension and the unreacted particles are reused in a suspension after being magnetically separated.

These characteristics make the described iron oxide particles especially useful in eliminating hydrogen sulfide from drilling muds. Typically, the iron oxide particles are suspended in a water based drilling mud in a quantity substantially in excess over that required to react the $H_2S$ expected to be encountered. The mud with its suspended particles is circulated through the drilled formation, reacting with hydrogen sulfide encountered, and returns laden with non-magnetic particulate product of reaction as well as the abrasive solids such as sand and drilling cuttings. Thereafter, substantially all of the particulate matter is concentrated onto a first portion of the drilling mud; while the remaining, substantially particulate-free portion of the mud (herein referred to as the "second portion") is retained for re-use. The first concentrated portion of the drilling mud is then passed through a magnetic separator. Substantially all, or at least a greater portion, of the excess unreacted iron oxide particles are separated out from the mud and are collected for re-use. The particulate product of reaction and other abrasive solids are next separated from the first portion of the mud by a conventional solids separator. The now substantially particulate-free first portion of the drilling mud is recombined with the second portion, above referred to, in readiness for re-circulation. The magnetically separated iron oxide particles are re-suspended in the mud together with a quantity of new reactive ferri-magnetic iron oxide particles, in order to restore the drilling mud's hydrogen sulfide scavenging ability.

To scavenge contaminating $H_2S$ from oil, an excess quantity of the described iron oxide particles is mixed into suspension, for reaction. Next, the hydrocarbon liquid containing the excess iron oxide particles, which remain unreacted, the particulate product of reaction and any other solids, is passed through a magnetic separator. These unreacted iron oxide particles so separated by the magnetic separator are collected for re-use. Electrostatic precipitation eliminates the remaining particulate matter from the hydrocarbon liquid. The oil is now scavenged, particulate-free and ready for utilization.

To scavenge waste water or geothermal water, an excess quantity of the described iron oxide particles is suspended in it. A concentration step follows; for example, the water may be diverted to a settling pond equipped with a weir; so that on settling, substantially all particulate matter is concentrated into a first portion of the water. This portion is passed through a magnetic separator, and, by it, the excess unreacted iron oxide particles are separated from the water, for re-use of these particles. If the water is to be used, the particulate product of reaction and any other solids are then separated out by utilizing a conventional solids separator. Likewise, the second substantially particulate-free portion of the water may be used or discharged.

BEST MODE FOR CARRYING OUT THE INVENTION

The particle utilized in practicing this invention are preferably the synthetic $Fe_3O_4$ particles disclosed in U.S. Pat. No. 4,008,775. Their average size is approximately six to eight microns. Though identified by X-ray diffraction as crystalline $Fe_3O_4$, ESCA/AUGER spectroscopy analysis indicates a surface coating of amorphous $Fe_2O_3$; this composition along with the extraordinarily large effective surface area of the synthetic particles may account for their exceptional reactivity. Such particles are referred to in this disclosure as $Fe_3O_4$.

The described synthetic $Fe_3O_4$ particles are considered to be ferrimagnetic, in the sense that while they are responsive to a magnetic force they do not become permanently magnetized by it. Thus, after being magnetically separated and collected, the particles separate readily from each other and are readily re-suspended in a liquid.

As disclosed in said U.S. Pat. No. 4,008,775 these iron oxide particles react with $H_2S$ to form a particulate product of reaction which is environmentally safe. This particulate product of reaction is also substantially non-magnetic.

In the process of the present invention, speedy and safe scavenging is effected by employing in suspension an excess quantity of the particles, and then effectively differentiating between the unreacted excess particles, which remain magnetic, and the reacted non-magnetic particles. As shown in the issued patent referred to, the particulate product of reaction is principally $FeS_2$ and may include other non-magnetic substantially stable iron-sulphur compounds, all of which reaction products are generally referred to in this disclosure as $FeS_2$. The reaction with $H_2S$ may initiate within the amorphous $Fe_2O_3$ and proceed into the crystalline core portion; the principal reaction occuring in the core appears to be essentially $Fe_3O_4 + 6H_2S \rightarrow 3FeS_2 + 4H_2O + 2H_2$.

Tests of magnetic recovery of the defined iron oxide particles were made by an independent test laboratory, which reported as follows:

The equipment used was an Eriez (trademark) Laboratory Wet Drum, Model L-8, adjusted to give equivalent recoveries of a 1,000 gauss high gradient wet drum and an Eriez (trademark) Laboratory Wet High Intensity Magnetic Separator (WHIMS), Model L-4, equipped with medium expanded metal collection matrix.

The test procedures were as follows:

About 2 kg of sample iron oxide particles were slurried in water and passed through the laboratory wet drum. The slurry was about 10% solids. The non-magnetics were filtered and then washed through the L-4 with the background field set to 8,000 gauss. All final products were filtered, dried and weighed.

The tests were evaluated as follows:

At standard concentrations, this sample showed a 99.3% recovery on the wet drum. This indicates that the recovery curves for more dilute slurries will follow a standard recovery curve for wet drums. The standard recovery curve shows an 85% to 88% recovery in the concentration range of 9 grams per gallon (1 pound per 50 gallons). This curve also shows that the recovery would be less than 5% when the concentration drops to 0.54 grams per gallon (1 pound per 840 gallons).

Use in drilling muds:

One of the dangers of drilling wells is that unexpectedly large concentrations of hydrogen sulfide may be encountered. These concentrations are sometimes deadly. The possibility such a concentration may be encountered warrants the use, in the drilling mud, of a quantity of the scavenger much greater than may actually be reacted. The described iron oxide particles have excellent rheological properties so that they may serve, in whole or in part, as the weighting agent.

For use in drilling mud the described iron oxide particles are suspended in the drilling mud in amounts ranging normally up to twenty pounds per barrel. The drilling mud, containing the excess quantity of iron oxide particles, is circulated through a drill bit and carries therefrom abrasive solids such as sand and drill cuttings, the particulate product of reaction with hydrogen sulfide, generally referred to as $FeS_2$ and the excess substantially unreacted iron oxide particles, $Fe_3O_4$. The quantity of $FeS_2$ formed is greater in weight than the quantity of reagent $Fe_3O_4$ particles; and since the abrasive solids were not theretofore present in the mud, the weight composition and rheological properties of the drilling mud may be altered on circulation and use.

Drilling mud properties are considered critical to the drilling process. By the following extractions and additions, the circulated used drilling mud may be substantially freed of sand, drill cuttings, and particulate product of reaction and restored to its original composition and rheology, again containing the chosen quantity of reactive iron oxide particles.

On rising to the surface, the used drilling mud is first passed through a screen of convenient size, roughly between 35 mesh and 100 mesh, to eliminate the larger drill cuttings, etc. The mud is then preferably passed through a cyclone type separator; by subjecting the drilling mud to a centrifugal force, substantially all of the particulate matter is concentrated into a first portion, for example 10% or less, of the drilling mud. The second particulate-free portion of the drilling mud, including any colloids used, is retained for re-use. This extraction and concentration reduces the volume of liquid and particulate matter to be passed through the next magnetic separation step, which may make feasible the use of a smaller capacity magnetic separator or increase its effectiveness.

On passing the concentrated first portion of the used drilling mud, containing the particulate matter, through the magnetic separator, at least a greater portion of the substantially unreacted iron oxide particles will be separated out of the drilling mud. These particles so extracted are collected for re-use. The extent of the extraction is dependent upon such factors as the efficiency with which the drilling mud is brought into contact with the magnetic separator; practical considerations are the capacity of the separator and the flow rate and viscosity of the liquid.

After the magnetic separation, there are further separated from this first portion of the drilling mud the abrasive solids and the particulate product of reaction formed; any conventional solids separation process may be used, such as sedimentation or centrifuging. This last extraction renders the first portion of the drilling mud substantially free of particulate matter. The retained second portion of the drilling mud, containing such colloids as were used, is re-combined with the first portion of the drilling mud. The salvaged iron oxide particles are then returned to the re-combined drilling mud, and a quantity of new iron oxide particles is also added, restoring the chosen quantity of magnetic iron oxide particles to the drilling mud, and thus restoring its ability to scavenge hydrogen sulfide. The fluid is now ready for re-use; and this process is repeated upon continuing re-circulation. The reacted particles, as well as any of the fluid not re-used, are environmentally safe and may be discharged or disposed of by conveying to a simple waste heap.

Valuable components of drilling muds are sometimes salvaged after drilling is completed, for re-use elsewhere. To do so is especially worthwhile where as here, an excess of reactive particles is used. On completion of drilling, the excess unreacted iron oxide particles may be magnetically separated as above described and salvaged for re-use elsewhere. Accordingly, although the reactive particles are employed in an excess amount during drilling, to provide a margin of safety in the event of unexpected large emissions of hydrogen sulfide, the process is economical because the unreacted particles are separated from all sand and drill cuttings and salvaged for re-use.

Use in hydrocarbon liquids:

If the contaminated liquid is a hydrocarbon liquid, this process will provide effective scavenging, whether the hydrocarbon liquid is crude or refined oil.

A quantity of ferri-magnetic iron oxide particles are suspended in the contaminated hydrocarbon liquid. This quantity is in excess over that required to react the hydrogen sulfide, thus speeding the reaction time.

Scavenging of hydrogen sulfide contained in anhydrous non-aqueous liquids is described in my co-pending application, above referred to, and the considerations given to mixing and agitation are applicable here.

After reaction of the hydrogen sulfide has occurred, the hydrocarbon liquid, containing the excess unreacted ferri-magnetic iron oxide particles, the non-magnetic particulate product of reaction and any other solids, is passed through a magnetic separator. Substantially all, or at least a greater portion of the unreacted iron oxide particles is separated out of the hydrocarbon liquid and collected for re-use.

The non-particulate product of reaction and any other solids are next separated out of the hydrocarbon liquid by use of any conventional solids separation process, such as sedimentation or centrifuging, or, for even greater effectiveness, electrostatic precipitation. These environmentally safe solids may be disposed of simply, as on an open waste heap. After this last extraction, the hydrocarbon liquid is thoroughly scavenged, environmentally safe, substantially particulate-free and is ready for utilization.

Use in water:

If the contaminated liquid is water, such as industrial waste water or condensed geothermal steam, the described ferri-magnetic particles are suspended in the water containing the hydrogen sulfide. The quantity of iron oxide particles so added to the contaminated water is in excess of that required to react the hydrogen sulfide present, thus to assure quick and effective scavenging. The hydrogen sulfide particles are contacted and reacted by the described ferri-magnetic iron oxide particles, forming the non-magnetic particulate product of reaction. In order to speed the reaction time the water may be agitated.

After effective scavenging has occurred, all the particulate may be concentrated in a first portion of the water small enough to be processed by an economically sized magnetic separator. For such concentration any process may be used; for example, the water may be allowed to settle in a settling pond equipped with a weir. The remaining or second portion of the water, substantially particulate-free, will flow over the weir. On passing the first concentrated portion of the water through the magnetic separator, all or at least a greater portion of the unreacted ferri-magnetic iron oxide particles will be separated. The iron oxide particles so separated are collected for re-use.

If the water is to be then used, the non-particulate product of reaction and any other solids are then separated from this first portion of the water by any conventional solids separation process, as by diversion into a settling pond. Both portions of the water are then usable. Alternatively, the water, itself environmentally safe and containing the environmentally safe reaction product and other solids, may merely be discharged.

Even though some of the magnetically separated iron oxide particles may contain some reacted $FeS_2$ molecules, the correlation between reactivity of the particles and their magnetic characteristic is so great as to warrant the reference, in this disclosure and claims, to magnetically separable particles as being substantially unreacted.

Variations from the processes above described will be apparent to those skilled in the art. For example, if the present ferri-magnetic particles are used in a drilling fluid in combination with a conventional non-magnetic weighting agent such as barite, the described process will nevertheless be useful for salvaging and re-using the unreacted ferri-magnetic particles, as well as the colloids. The barite, being non-magnetic, will be separated out along with other non-magnetic particles, that is, the reacted particles, sand and drill cuttings. If it is determined that these non-magnetic particles taken together are not too abrasive to serve as a weighting agent along with a replenished quantity of unreacted particles and colloids, they may be so re-used; otherwise, such all separated non-magnetic solids should be discarded.

INDUSTRIAL APPLICABILITY

A principal use of the present invention is in scavenging hydrogen sulfide from drilling muds by the use of a quantity of the particulate iron oxide significantly in excess of that required to actually react the hydrogen sulfide, so as to provide a margin of safety. Magnetic recovery of the excess renders the process economical. Another justification for use of an excess is that the particles serve at least in part as a weighting agent.

I claim:

1. In scavenging hydrogen sulfide from a hydrogen sulfide contaminated liquid, the process of
   suspending in a hydrogen sulfide contaminated liquid a quantity of ferri-magnetic iron oxide particles of the type which react with hydrogen sulfide to form a substantially non-magnetic environmentally safe particulate product of reaction,
   said quantity being in excess over that required for the reaction of such hydrogen sulfide,
   contacting and reacting the hydrogen sulfide with the said iron oxide particles and thereby forming such non-magnetic environmentally safe particulate product of reaction, the excess iron oxide particles remaining substantially unreacted and retaining their ferri-magnetic characteristic, then
   (A) passing the liquid containing the particulate matter comprising the excess unreacted ferri-magnetic iron oxide particles, particulate product of reaction and any other solids, through a magnetic separator, and, by it, separating and recovering therefrom substantially all or at least the greater portion of the said unreacted iron oxide particles,
   (B) separating out from the liquid such non-magnetic particulate product of reaction, along with any solids present, whereby to dispose of same without hazard to the environment,
   (C) recovering the purified liquid and
   (D) returning the unreacted iron oxide particulates to the contaminated liquid treatment step.

2. In well drilling using a drilling fluid, the process of suspending in such drilling fluid a quantity of ferri-magnetic iron oxide particles of the type which react with hydrogen sulfide to form a substantially non-magnetic, environmentally safe particulate product of reaction, said quantity being in excess over that required for anticipated reaction with such hydrogen sulfide as may be encountered in drilling, circulating such drilling mud downward through a drill bit while drilling and then upward through such formation, thus incorporating drill cuttings into the drilling fluid and thus contacting and reacting, with the said iron oxide particles, any such hydrogen sulfide so encountered, whereby to form such non-magnetic environmentally safe particulate product of reaction, and leaving at least a substantial portion of said iron oxide particles substantially unreacted and retaining their ferri-magnetic characteristic, then (A) passing the drilling fluid, containing the particulate matter comprising the drill cuttings, unreacted ferri-magnetic iron oxide particles, and such particulate product of reaction, if any, through a magnetic separator, and, by it, separating and recovering therefrom substantially all or at least the greater portion of the said unreacted iron oxide particles, then (B) separating out from the drilling fluid substantially all the remaining particulate matter including drill cuttings and any such non-magnetic particulate product of reaction, whereby to dispose of same without hazard to the environment, (C) recovering a particulate-free drilling fluid portion, and then (D) returning, to said particulate-free drilling fluid portion, said separated unreacted ferri-magnetic particles and such additional quantity of such ferri-magnetic particles as may be substantially equal to such quantity, if any, of the non-magnetic particulate product of reaction.

* * * * *